United States Patent
Khasnobish et al.

(10) Patent No.: US 11,666,227 B2
(45) Date of Patent: Jun. 6, 2023

(54) METHOD AND SYSTEM FOR OPTIMUM CHANNEL SELECTION IN TWIN RADAR FOR CARDIOPULMONARY SIGNAL MONITORING

(71) Applicant: TATA CONSULTANCY SERVICES LIMITED, Mumbai (IN)

(72) Inventors: Anwesha Khasnobish, Kolkata (IN); Raj Rakshit, Kolkata (IN); Smriti Rani, Kolkata (IN); Andrew Gigie, Bangalore (IN); Tapas Chakravarty, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 311 days.

(21) Appl. No.: 17/009,179

(22) Filed: Sep. 1, 2020

(65) Prior Publication Data
US 2021/0121076 A1    Apr. 29, 2021

(30) Foreign Application Priority Data
Oct. 25, 2019 (IN) .............................. 201921043573

(51) Int. Cl.
*A61B 5/0205* (2006.01)
*A61B 5/00* (2006.01)

(52) U.S. Cl.
CPC .......... *A61B 5/0205* (2013.01); *A61B 5/7225* (2013.01); *A61B 5/7246* (2013.01); *A61B 5/7257* (2013.01)

(58) Field of Classification Search
CPC ... A61B 5/0205; A61B 5/7225; A61B 5/7246; A61B 5/7257; A61B 5/7228;
(Continued)

(56) References Cited

U.S. PATENT DOCUMENTS

| 2005/0197549 A1* | 9/2005 | Baker ................. A61B 5/7203 600/323 |
| 2008/0077015 A1 | 3/2008 | Boric-Lubecke et al. |

(Continued)

OTHER PUBLICATIONS

Ebrahim et al., "A Doppler Radar System for Sensing Physiological Parameters in Walking and Standing Positions", Sensors, 17, Mar. 1, 2017 (Year: 2017).*

(Continued)

*Primary Examiner* — Eric F Winakur
*Assistant Examiner* — Jonathan Drew Moroneso
(74) *Attorney, Agent, or Firm* — Finnegan, Henderson, Farabow, Garrett & Dunner, LLP

(57) ABSTRACT

This disclosure relates to selection of optimum channel in twin radars for efficient detection of cardiopulmonary signal rates. State-of-the-art solutions involve use of IQ (In-phase and Quadrature) channel radar which need continuous calibration. Distance of the radar from a subject being monitored affects performance. The present disclosure enables enhanced cardiopulmonary signal rate monitoring using a time domain approach, wherein only the data from signal reflected off the radar is considered. The solution is also time window adaptive. Signal property and radar physics-based methods have been implemented for selecting an optimum channel in twin radars thereby enhancing detection of respiration rate and breath rate.

9 Claims, 12 Drawing Sheets

(58) Field of Classification Search
CPC . A61B 5/02444; A61B 5/0245; A61B 5/0255; A61B 5/0816; A61B 5/1114; A61B 5/1135; A61B 5/7221; A61B 5/0507; A61B 2505/07; A61B 2562/0228; G01S 7/354; G01S 7/415; G01S 13/536; G01S 13/88
See application file for complete search history.

(56) References Cited

U.S. PATENT DOCUMENTS

| | | | |
|---|---|---|---|
| 2017/0296104 A1* | 10/2017 | Ryan | A61B 5/1118 |
| 2019/0069840 A1* | 3/2019 | Young | A61B 5/0022 |
| 2022/0142478 A1* | 5/2022 | Bliss | A61B 5/02405 |

OTHER PUBLICATIONS

Gigie, Andrew et al., "*Novel Approach for Vibration Detection Using Indented Radar*", Progress In Electromagnetics Research C, Jul. 17, 2018, vol. 87, Progress In Electromagnetics Research, http://www.jpier.org/PIERC/pierc87/13.18071702.pdf.

Sveistrup, Brian et al., "*An experimental vital signs detection radar using low-IF heterodyne architecture and single-sideband transmission*", 2013 IEEE International Wireless Symposium (IWS), Apr. 14-18, 2013, IEEE, https://backend.orbit.dtu.dk/ws/files/73779394/06616752.pdf.

* cited by examiner

METHOD AND SYSTEM FOR OPTIMUM CHANNEL SELECTION IN TWIN RADAR FOR CARDIOPULMONARY SIGNAL MONITORING

PRIORITY CLAIM

This U.S. patent application claims priority under 35 U.S.C. § 119 to: Indian Patent Application No. 201921043573, filed on 25 Oct. 2019. The entire contents of the aforementioned application are incorporated herein by reference.

TECHNICAL FIELD

The disclosure herein generally relates to monitoring cardiopulmonary signals, and, more particularly, to selecting an optimum channel in a twin radar for cardiopulmonary signal monitoring.

BACKGROUND

Doppler radars have been used for detecting respiration rate of a human being without compromising safety and privacy of the person considering they are positioned at a distance from the subject being monitored. Also, temperature, humidity, clothing worn by the subject, or such factors do not affect the monitoring of the subject. The small angle approximation techniques of phase demodulation of Continuous Wave (CW) Doppler radar for detecting very minute respiratory-chest wall movements suffer from inherent optimum-null point problem. This in turn hinders accurate respiratory rate or breathing rate (BR) or heart rate (HR) computations. Cardiopulmonary rate is a precursor for the onset of many ailments ranging from anxiety to lung and heart ailments. It is also a biomarker for cognitive activities, physical as well as mental workload and stress. Hence it is pertinent that cardiopulmonary rate be accurately computed.

SUMMARY

Embodiments of the present disclosure present technological improvements as solutions to one or more of the above-mentioned technical problems recognized by the inventors in conventional systems.

In an aspect, there is provided a processor implemented method for optimum channel selection in a twin radar characterized by a first channel and a second channel, the method comprising the steps of: receiving a time domain signal reflected from a subject being monitored, by each of the first channel and the second channel respectively; filtering, by a low pass filter, the time domain signal received by each of the first channel and the second channel respectively, to obtain a filtered time domain signal having frequencies less than a predetermined frequency corresponding to restful breathing associated with the subject being monitored; simultaneously computing, via one or more hardware processors, a peak to peak value ($A_{PP1}$) of an autocorrelation function (ACF) of the filtered time domain signal associated with the first channel and the second channel respectively, for a predefined time window; and an average value ($V_{PP1}$) of peak to peak amplitude of the filtered time domain signal associated with the first channel and the second channel respectively, for the predefined time window; and selecting, via the one or more hardware processors, either the first channel or the second channel as the optimum channel based on the computed peak to peak value of the ACF and the average value of the peak to peak amplitude of the filtered time domain signal.

In another aspect, there is provided a system for optimum channel selection in a twin radar characterized by a first channel and a second channel, the system comprising: one or more data storage devices operatively coupled to one or more hardware processors and configured to store instructions configured for execution via the one or more hardware processors to: receive a time domain signal reflected from a subject being monitored, by each of the first channel and the second channel respectively; filter, by a low pass filter, the time domain signal received by each of the first channel and the second channel respectively, to obtain a filtered time domain signal having frequencies less than a predetermined frequency corresponding to restful breathing associated with the subject being monitored; simultaneously compute: a peak to peak value ($A_{PP1}$) of an autocorrelation function (ACF) of the filtered time domain signal associated with the first channel and the second channel respectively, for a predefined time window; and an average value ($V_{PP1}$) of peak to peak amplitude of the filtered time domain signal associated with the first channel and the second channel respectively, for the predefined time window; and select either the first channel or the second channel as the optimum channel based on the computed peak to peak value of the ACF and the average value of the peak to peak amplitude of the filtered time domain signal.

In yet another aspect, there is provided a computer program product comprising a non-transitory computer readable medium having a computer readable program embodied therein, wherein the computer readable program, when executed on a computing device, causes the computing device to: receive a time domain signal reflected from a subject being monitored, by each of the first channel and the second channel respectively; filter, by a low pass filter, the time domain signal received by each of the first channel and the second channel respectively, to obtain a filtered time domain signal having frequencies less than a predetermined frequency corresponding to restful breathing associated with the subject being monitored; simultaneously compute: a peak to peak value ($A_{PP1}$) of an autocorrelation function (ACF) of the filtered time domain signal associated with the first channel and the second channel respectively, for a predefined time window; and an average value ($V_{PP1}$) of peak to peak amplitude of the filtered time domain signal associated with the first channel and the second channel respectively, for the predefined time window; and select either the first channel or the second channel as the optimum channel based on the computed peak to peak value of the ACF and the average value of the peak to peak amplitude of the filtered time domain signal.

In accordance with an embodiment of the present disclosure, the one or more processors are further configured to select either the first channel or the second channel as the optimum channel by: comparing the peak to peak value ($A_{PP1}$) associated with the first channel and the second channel, respectively and selecting a channel associated with a higher peak to peak value of the ACF as a first potential optimum channel; comparing the average value ($V_{PP1}$) associated with the first channel and the second channel, respectively and selecting a channel associated with a higher average value of the peak to peak amplitude of the voltage signal as a second potential optimum channel; and performing one of: if the first potential optimum channel and the second potential optimum channel are identical, selecting an associated channel as the optimum channel; or computing variance of peak amplitudes associated with the first potential optimum channel and the second potential optimum channel and selecting a channel associated with a lesser variance of peak amplitudes as the optimum channel.

In accordance with an embodiment of the present disclosure, the one or more processors are further configured to perform spectrum analyses on the selected optimum channel to obtain breathing rate of the subject being monitored by: transforming the filtered time domain signal associated with the selected optimum channel to a frequency domain signal using a Fast Fourier transform (FFT) method; and obtaining the breathing rate of the subject being monitored in breaths per minute, based on a frequency associated with a highest peak of the frequency domain signal.

In accordance with an embodiment of the present disclosure, the one or more processors are further configured to perform spectrum analyses on the selected optimum channel to obtain heart rate of the subject being monitored by: filtering the time domain signal received by the selected optimum channel, by a band pass filter to obtain a filtered time domain signal having frequencies in a predetermined range corresponding to restful heart rate range associated with the subject being monitored; transforming the filtered time domain signal associated with the selected optimum channel to a frequency domain signal using a Fast Fourier transform (FFT) method; and obtaining the heart rate of the subject being monitored in beats per minute, based on a frequency associated with a highest peak of the frequency domain signal.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
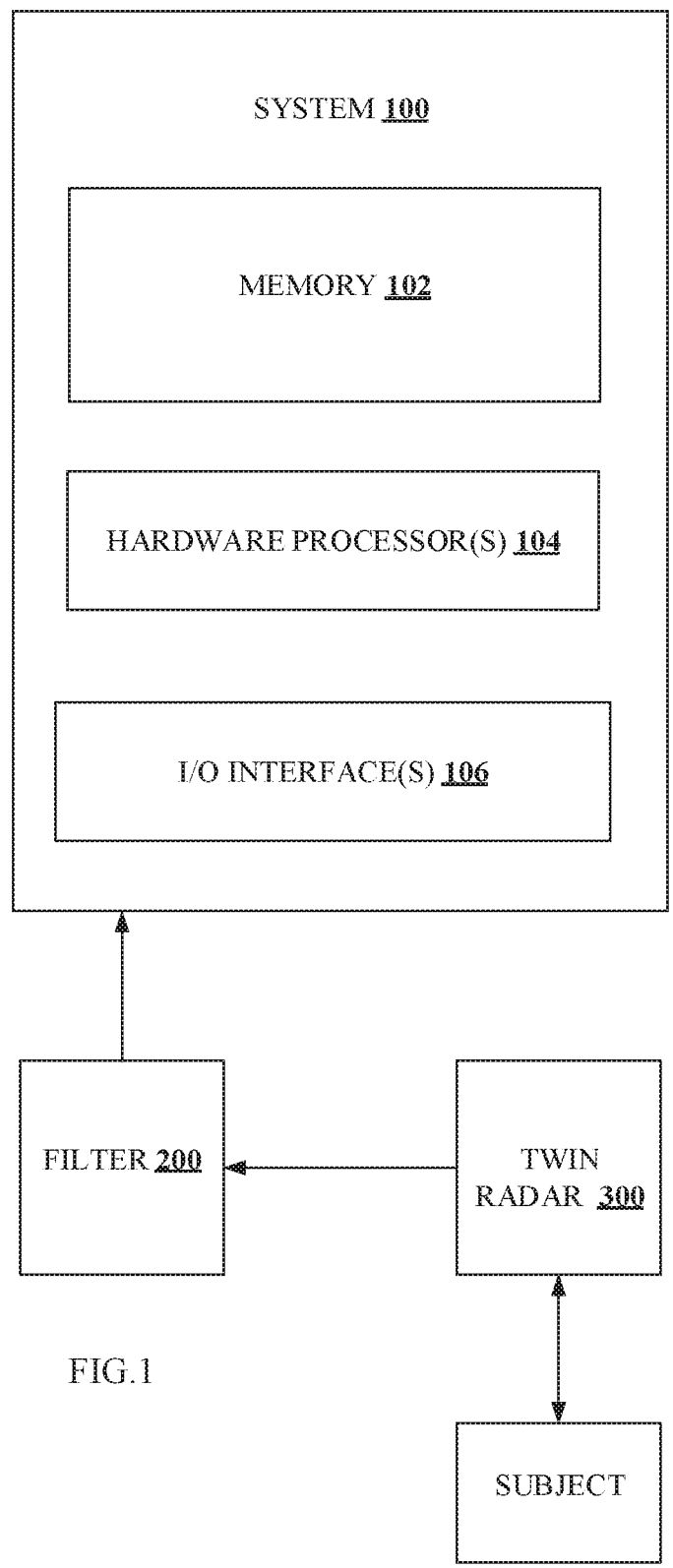
FIG. 1 illustrates an exemplary block diagram of a system for optimum channel selection in a twin radar for cardiopulmonary signal monitoring, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Considering the significance of cardiopulmonary signal monitoring to timely detect lung or heart ailments, Doppler radars have been gaining traction as a means to measure breathing rate. Radars are unaffected by ambient light conditions and there are no privacy issues associated as seen in vision-based approaches. Since radar-based approaches are unobtrusive, they can be implemented for continuous cardiopulmonary signal monitoring of infants, elderly people, patients and even for animal care.

Continuous Wave (CW) radars provide hardware simplicity and works with simple signal processing techniques. However, CW radars measure velocity of the target only. In the present disclosure, phase difference between continuously transmitted and received signal of a CW radar is demodulated to obtain the rate at which the chest wall moves due to respiration or heart rate. Phase of the baseband signal of a CW radar is a sinusoidal function of the summation of the distance from the subject and its chest wall movement. In the context of the present disclosure, the expression 'subject' refers to a living being such as a human or an animal. The amplitude of chest wall movement, corresponding to the displacement due to respiration is small as compared to the carrier wavelength of a radar. Thus, small angle approximation technique can be used for phase demodulation. Optimum detection occurs when the phase shift due to distance from the subject $\theta_0$ is an odd multiple of $\pi/2$. The baseband output becomes a linear function of time varying chest wall movement. Conversely for $\theta_0$ being an even multiple of $\pi/2$, null detection occurs. These null and optimum points alternate by a distance of one-eighth ties the transmitting wavelength $\lambda$ of the radar.

State-of-the-art uses extra hardware or an IQ (In-phase and Quadrature) channel radar along with signal processing techniques. The techniques are plagued by either IQ imbalances or need continuous calibration. A simple and cost-effective solution was provided by the Applicant in Indian Patent Application No. 201821038470 titled 'Real Time Unobtrusive Monitoring Of Physiological Signals', wherein a dual radar setup referred as indented radar was disclosed. The indented radar employs optimum spatial placement of two single channel CW radars to compensate for the optimum-null point problem and to have the two single channel CW radars behaving as pseudo I and Q radars respectively. The system disclosed consists of placing two single channel radars, such that the optimum point of one radar is placed at the null point of the other radar, in order to get high fidelity data at any given distance. Depending on the position of the subject with respect to the dual radar setup, any one of the channels maybe null or optimum. However, for a non-rigid subject like a human sitting in front of the indented radar, constant and automated null and optimum channel selection is a requisite for accurately monitoring cardiopulmonary signals. This problem is augmented by the fact that a physiological signal such as breathing rate is of very low frequency, low bandwidth and low amplitude. Due to the specific characteristic of the signal under consideration, a lot of frequency domain analysis have limitations, when applied to such a signal.

The present disclosure has addressed this issue by providing a data driven approach of automated selection of the optimum channel between the two channels of a twin radar or a dual channel radar. Although the technical problem was realized by the Applicant after providing the disclosure of Application no. 201821038470, it may be understood by a person skilled in the art, that the present disclosure may be applicable to a twin radar, in general, and is not limited to use of the indented radar of Application no. 201821038470. In the context of the present disclosure, the expression 'radar' refers to a twin radar characterized by a first channel and a second channel. Particularly, the first channel and the second channel are CW radars. A time domain approach which is time window adaptive, computationally inexpensive and demands no prior calibration either at the subject level or at the system level is provided.

Referring now to the drawings, and more particularly to FIGS. 1 through 8, where similar reference characters denote corresponding features consistently throughout the figures, there are shown preferred embodiments and these embodiments are described in the context of the following exemplary system and/or method.

FIG. 1 illustrates an exemplary block diagram of a system for optimum channel selection in a twin radar for cardiopulmonary signal monitoring, in accordance with some embodiments of the present disclosure. In an embodiment, the system 100 is characterized by the state representation model and includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

In an embodiment, a twin radar 300 is characterized by the first channel and the second channel, each being configured to transmit and receive a time domain signal reflected from the subject being monitored. In an embodiment, a filter 200 may be at least one of a low pass filter or a band pass filter depending on whether the breathing rate or the heart rate of the subject is being monitored as described later herein below. Furthermore, in an embodiment, the filter 200 may be part of the system 100, wherein the one or more hardware processors 104 may be configured to serve as the filter 200.

Figure 2:
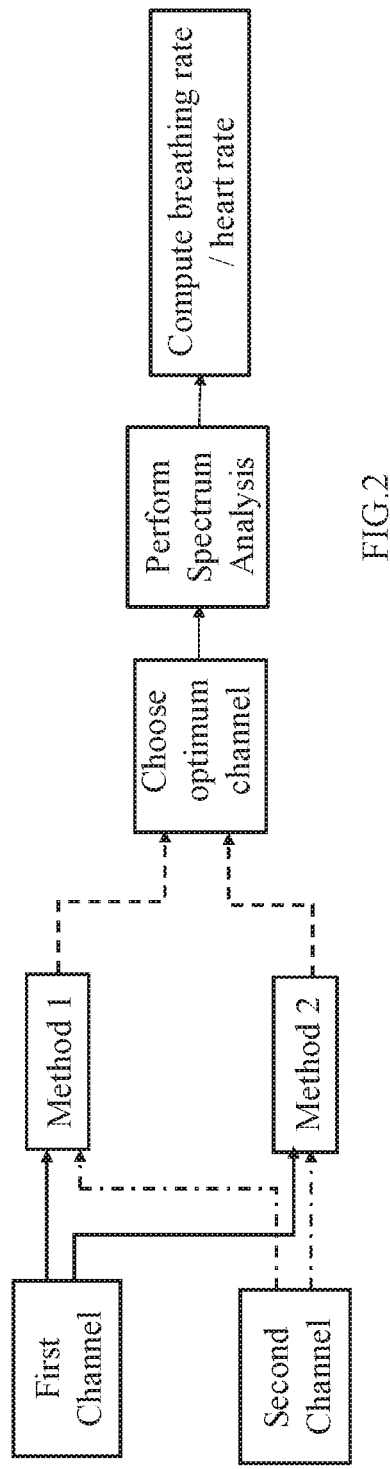
FIG. 2 illustrates a high-level flow chart of a method for optimum channel selection in the twin radar for cardiopulmonary signal monitoring, in accordance with some embodiments of the present disclosure.

FIG. 2 illustrates a high-level flow chart of a method for optimum channel selection in the twin radar for cardiopulmonary signal monitoring. For each pre-defined time window, two methods (method 1 and method 2) are employed simultaneously to select an optimum channel amongst the first channel and the second channel of the twin radar. Once the optimum channel is selected, breathing rate or heart rate of the subject being monitored may be computed by performing a spectrum analysis.

Figure 3A:
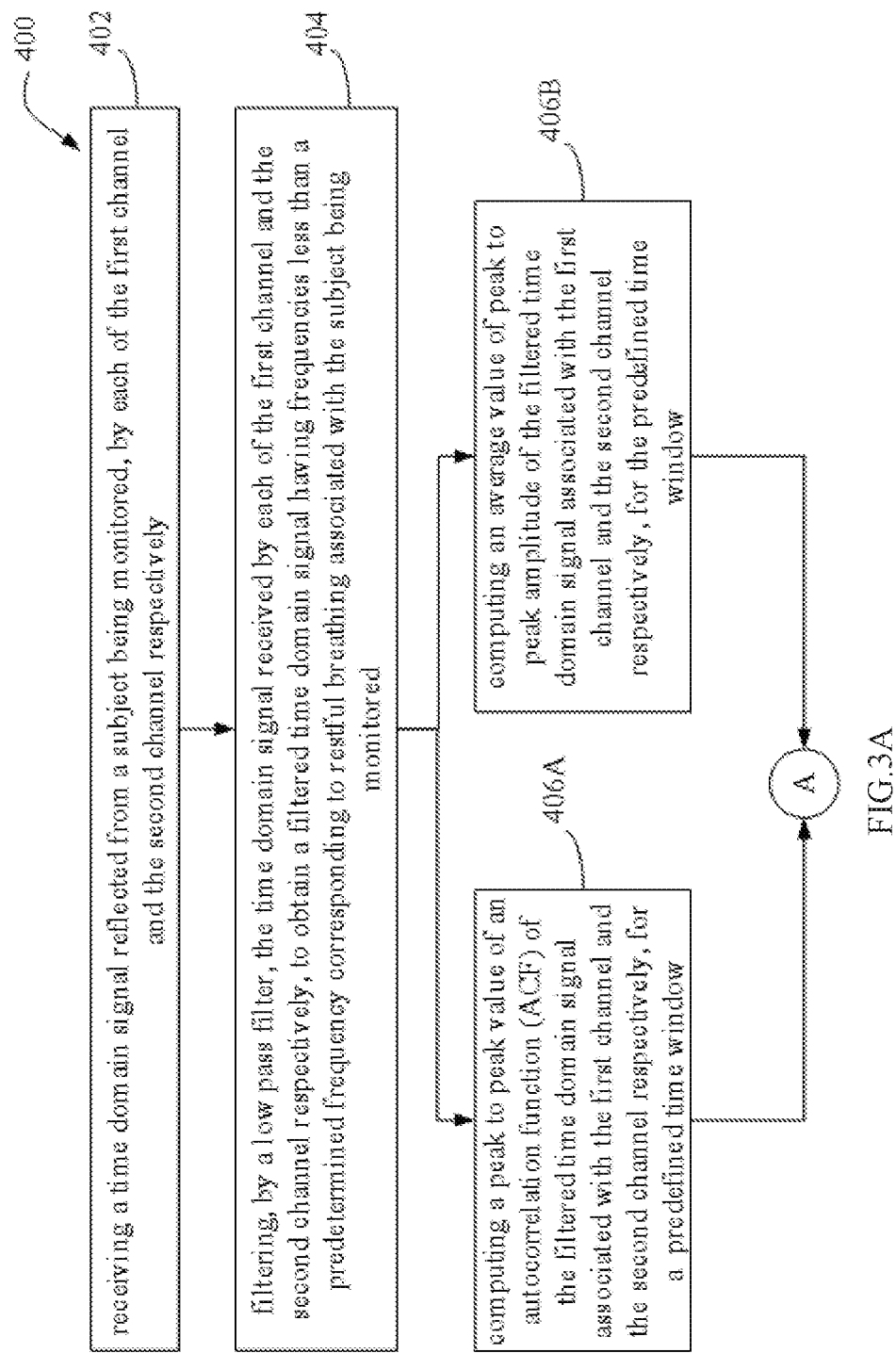
FIG. 3A through FIG. 3B illustrate an exemplary flow diagram of a computer implemented method for optimum channel selection in the twin radar for cardiopulmonary signal monitoring, in accordance with some embodiments of the present disclosure.
Figure 3B:
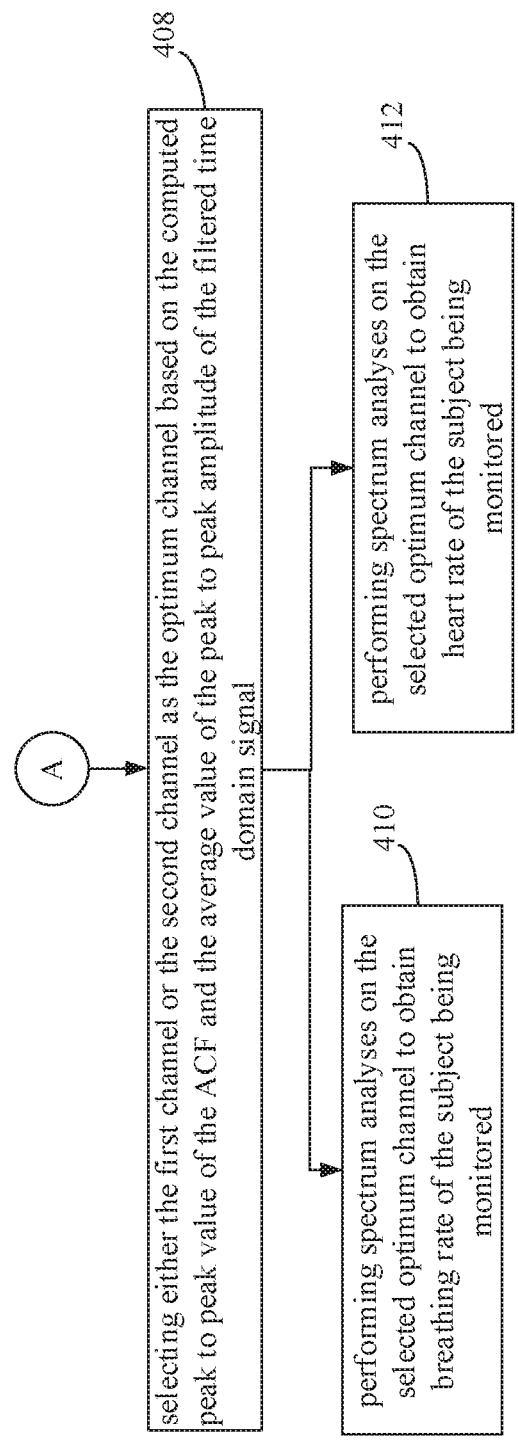

FIG. 3A through FIG. 3B illustrate an exemplary flow diagram of a computer implemented method 400 for optimum channel selection in the twin radar for cardiopulmonary signal monitoring, in accordance with some embodiments of the present disclosure. In an embodiment, the system 100 includes one or more data storage devices or memory 102 operatively coupled to the one or more processors 104 and is configured to store instructions configured for execution of steps of the method 400 by the one or more processors 104. The steps of the method 400 will now be explained in detail with reference to the high-level flow chart of FIG. 2 and the components of the system 100 of FIG. 1. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

In accordance with an embodiment of the present disclosure, the one or more processors 104 are configured to receive, at step 402, a time domain signal reflected from the subject being monitored, by each of the first channel and the second channel respectively. Further at step 404, the time domain signal received by each of the first channel and the second channel respectively, are filtered by the filter 200. In an embodiment, the filter utilized at step 404 is a low pass filter that filters the time domain signal to obtain a filtered time domain signal having frequencies less than a predetermined frequency corresponding to restful breathing associated with the subject being monitored. In an embodiment, if the subject is a human being, the restful breathing and accordingly, the predetermined frequency is 0.5 Hz.

In accordance with an embodiment of the present disclosure, the one or more processors 104 are configured to simultaneously compute, at step 406, the method 1 and the method 2 referred in FIG. 2 before. Breathing signal of a healthy subject at rest is highly periodic. The optimum channel reproduces the fundamental frequency, whereas null channel picks a lot of harmonics and noise. Thus, at any time, the signal of optimum channel will be more autocorrelated than the null channel. This understanding forms the basis of method 1 for distinguishing between the null and optimum channel. The method 1 accordingly involves computing, at step 406A, a peak to peak value ($A_{PP1}$) of an autocorrelation function (ACF) of the filtered time domain signal associated with the first channel and the second channel respectively, for the predefined time window. For a waveform g(t), existing in an interval $T_1$ to $T_2$, the autocorrelation function $\emptyset_{gg}(\tau)$, for a lag $\tau$, is given by equation (1) below.

$$\emptyset_{gg}(\tau) = \int_{T_1}^{T_2} g(t)g(t+\tau)dt \quad (1)$$

Generally, a breath cycle is 3 to 4 seconds. If the time window is less than 15 seconds, it is difficult to capture 2 to 3 breaths in a cycle. In accordance with the present disclosure, based on domain knowledge, the predefined time window is at least 15 seconds or multiples of 15 (30 seconds, 45 seconds, etc.).

Another differentiating property of a time series signal of a null channel is its low peak to peak value of amplitude ($V_{pk-pk}$) as compared to that of an optimum channel. The method 2 involves computing, at step 406B, an average value ($V_{PP1}$) of peak to peak amplitude of the filtered time domain signal associated with the first channel and the second channel respectively, for the predefined time window.

In accordance with an embodiment of the present disclosure, the one or more processors 104 are configured to select, at step 408, either the first channel or the second channel as the optimum channel based on the computed peak to peak value of the ACF and the average value of the peak to peak amplitude of the filtered time domain signal.

In accordance with an embodiment of the present disclosure, the step of selecting either the first channel or the second channel as the optimum channel comprises comparing the peak to peak value ($A_{PP1}$) associated with the first channel and the second channel, respectively. The channel associated with a higher peak to peak value of the ACF is selected as a first potential optimum channel. Then, the average value ($V_{PP1}$) associated with the first channel and the second channel, respectively are compared. The channel associated with a higher average value of the peak to peak amplitude of the voltage signal is selected as a second potential optimum channel. If the first potential optimum channel and the second potential optimum channel are identical, there is no conflict, and an associated channel is selected as the optimum channel. Method 2 may give a false positive when sudden noisy peaks corrupt the average value ($V_{PP1}$). Accordingly, if there is a conflict and the first optimum channel identified by the method 1 and the second optimum channel identified by the method 2 are different, then variance of peak amplitudes associated with the first potential optimum channel and the second potential optimum channel are computed. For periodic signals, variance of peak amplitudes is less due to the absence of sudden noisy peaks. The channel associated with a lesser variance of peak amplitudes is then selected as the optimum channel.

Once the optimum channel in the twin radar is selected, either the breathing rate of the heart rate may be computed by performing spectrum analyses on the selected optimum channel. In accordance with an embodiment of the present disclosure, the one or more processors 104 are configured to obtain breathing rate of the subject being monitored, at step 410, by transforming the filtered time domain signal associated with the selected optimum channel to a frequency domain signal suing a Fast Fourier Transform (FFT) method. The breathing rate of the subject being monitored is obtained in breaths per minute based on a frequency associated with a highest peak of the frequency domain signal. In the scenario where the subject is a human being, the breathing rate is obtained as a product of the frequency and 60 (seconds).

In accordance with an embodiment of the present disclosure, the one or more processors 104 are configured to obtain heart rate of the subject being monitored, at step 412, by filtering the time domain signal received by the selected optimum channel, by the filter 200. In this scenario, the filter is a band pass filter configured to filter the time domain signal to obtain a filtered time domain signal having frequencies in a predetermined range corresponding to restful heart rate range associated with the subject being monitored. In the scenario where the subject is a human, the restful heart rate and accordingly the predetermined range is 1 Hz to 2 Hz. The filtered time domain signal associated with the selected optimum channel is transformed to a frequency domain using a Fast Fourier Transform (FFT) method. The heart rate of the subject being monitored is obtained in beats per minute, based on a frequency associated with the highest peak of the frequency domain signal. In the scenario where the subject is a human being, the heart rate is obtained as a product of the frequency and 60 (seconds).

Experimental Observations 17 subjects were requested to sit on a chair at a distance of about 70 cm from an indented radar system (twin radar disclosed in Application no. 201821038470). The twin radar has two single channel 10.525 GHz CW radars. Data was collected at a sampling rate of 50 Hz for 60 seconds. The subjects were asked to completely relax for 5 minutes and then data was acquired via NI DAQ (National Instruments Data Acquisition) and Labview (National Instruments product). The subjects wore normal garments (typically two layers of clothing) and were told to completely relax with eyes closed. To minimize motion artifacts, subjects were requested to avoid sudden movements. For ground truth, as well as surrounding clutter information, a video recording of the subjects was done while experimentation.

Signal pre-conditioning for each channel involved DC component removal followed by low pass filtering. Breathing rate for a normal healthy person ranges from 12 to 24 breaths per minute. So, the time domain signal was passed through a second order low pass filter of cut off frequency 0.5 Hz. All signal processing was done in Matlab 2018a. The method 400 was implemented on the data with different window lengths viz., 15 seconds, 30 seconds and 60 seconds. This was done to assess the best possible choice of computing the breathing rate. Hence in total, there were 68, 34 and 17 window segments of data respectively.

Figure 4A:
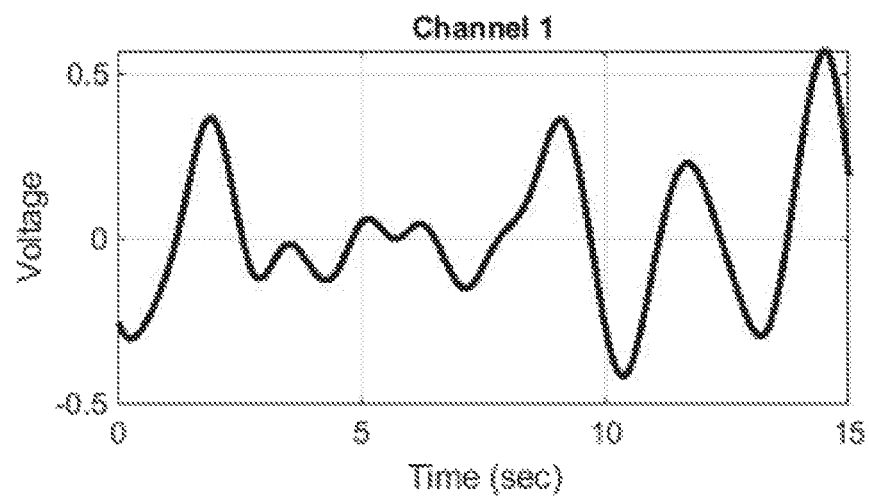
FIG. 4A and FIG. 4B illustrate a time domain signal, each received by a first channel and a second channel respectively of the twin radar.
Figure 4B:
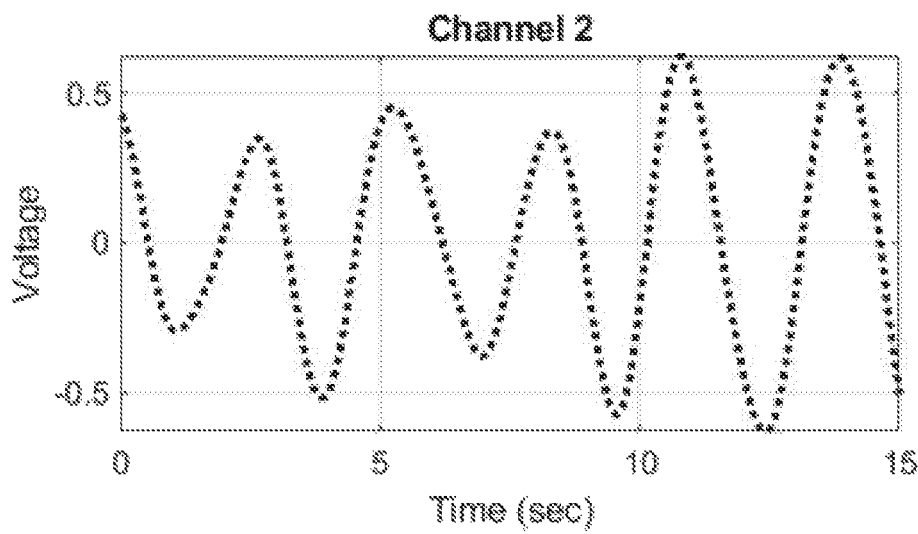
Figure 4C:
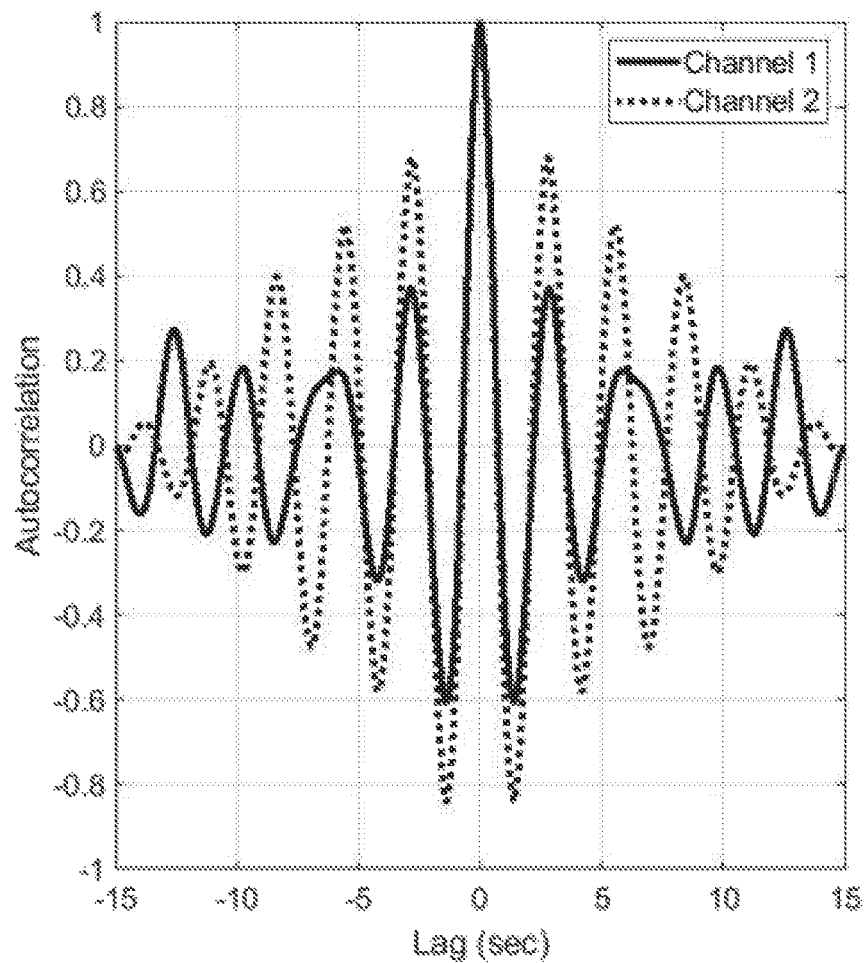
FIG. 4C illustrates autocorrelation of the time domain signals of FIG. 4A and FIG. 4B respectively, for a 15 second window, in accordance with some embodiments of the present disclosure.

FIG. 4A and FIG. 4B illustrate a time domain signal, each received by a first channel (represented as channel 1 in FIGS. 4,5,6,7) and a second channel (represented as channel 2 in FIGS. 4,5,6,7) respectively of the twin radar. FIG. 4C illustrates autocorrelation of the time domain signals of FIG. 4A and FIG. 4B respectively, for a 15 second window, in accordance with some embodiments of the present disclosure. It may be noted that the second channel has a higher periodicity and autocorrelation function clearly shows it. Accordingly, the second channel was chosen as the optimum channel.

Figure 5A:
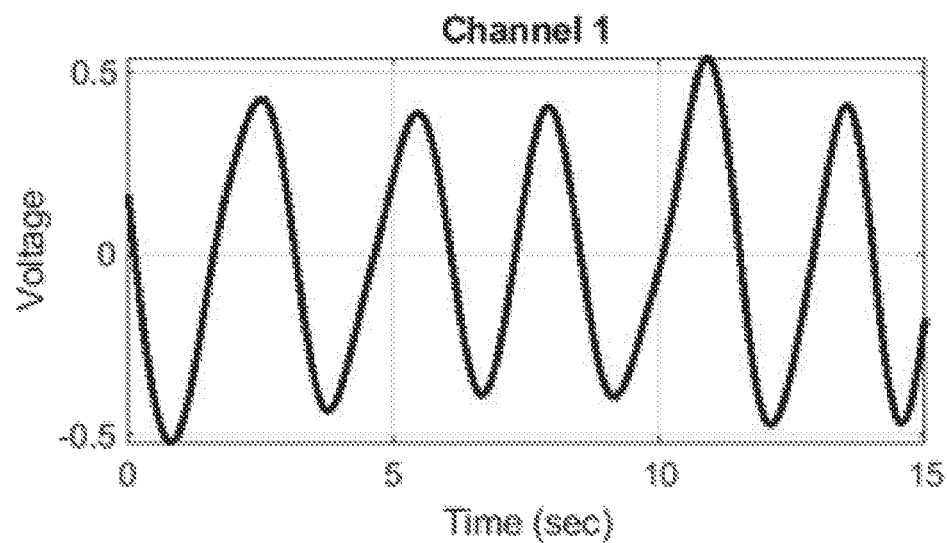
FIG. 5A and FIG. 5B illustrate a time domain signal, each received by the first channel and the second channel respectively of the twin radar.
Figure 5B:
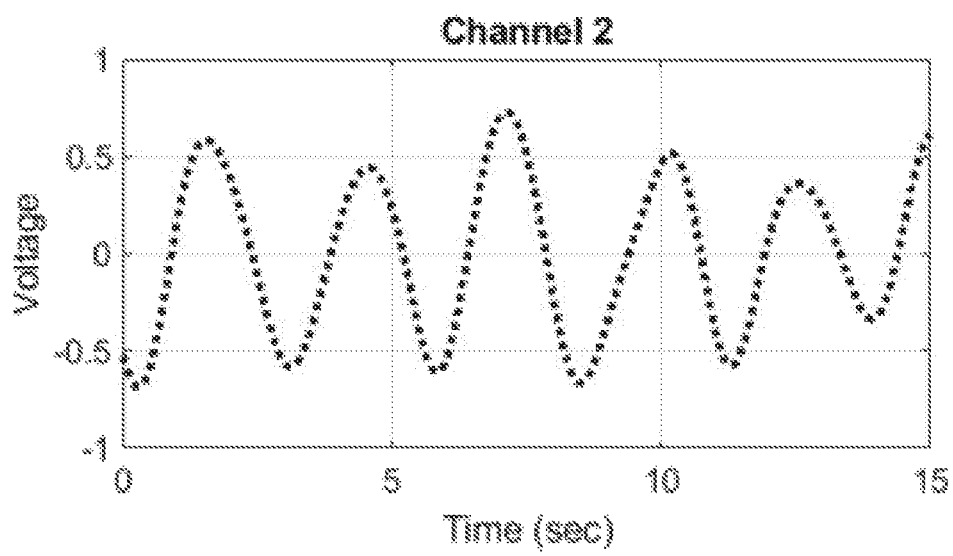
Figure 5C:
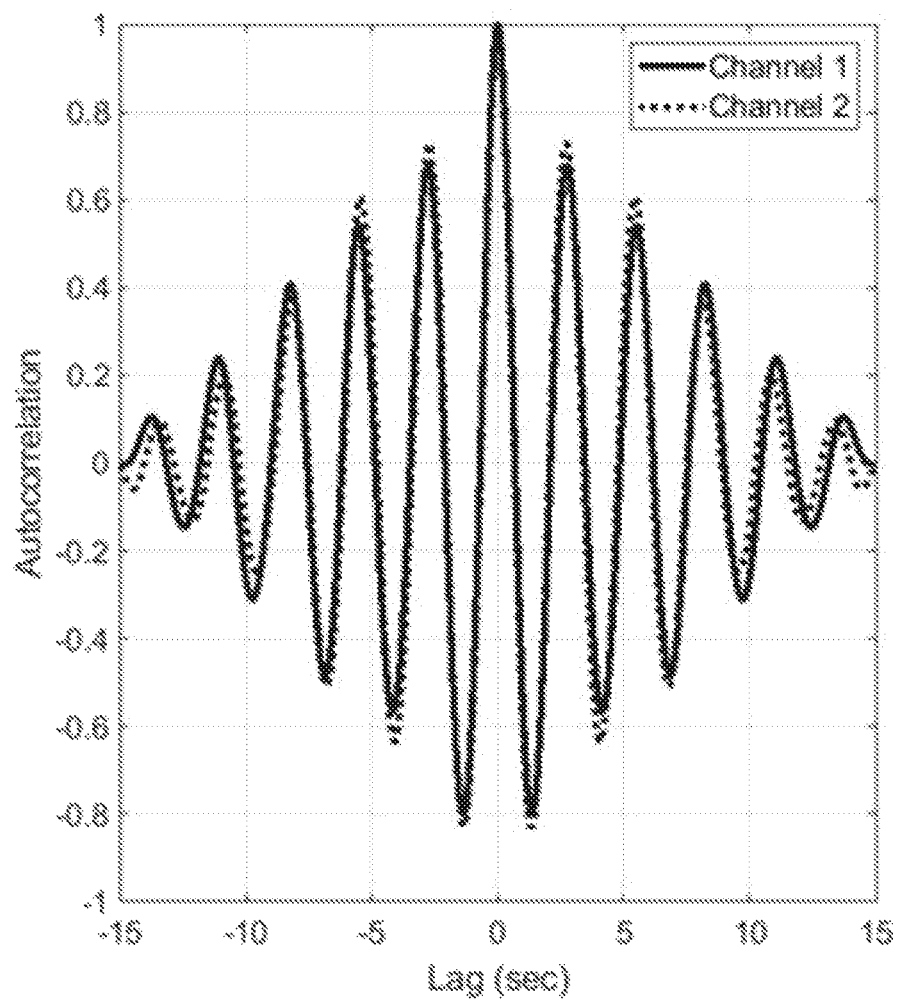
FIG. 5C illustrates autocorrelation of the time domain signals of FIG. 5A and FIG. 5B respectively, for a 15 second window, in accordance with some embodiments of the present disclosure, wherein the autocorrelation of the second channel is equal to the autocorrelation of the first channel.

FIG. 5A and FIG. 5B illustrate a time domain signal, each received by a first channel and a second channel respectively of the twin radar. FIG. 5C illustrates autocorrelation of the time domain signals of FIG. 5A and FIG. 5B respectively, for a 15 second window, in accordance with some embodiments of the present disclosure. The first channel and the second channel are between the optimum and the null position and thus the autocorrelation of the second channel is equal to the autocorrelation of the first channel. Accordingly, selecting either of the channels serves the purpose of monitoring cardiopulmonary signals.

Figure 6A:
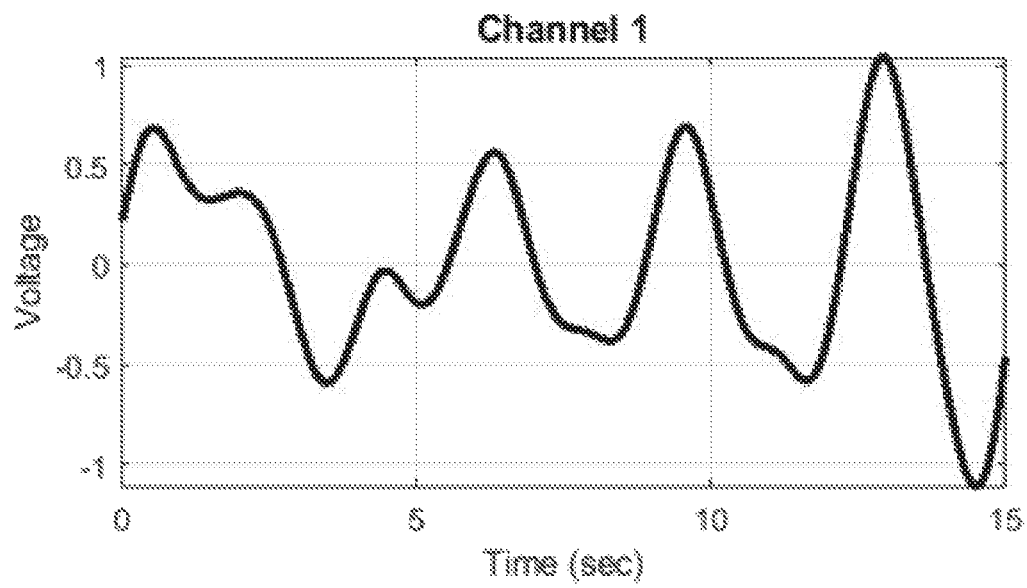
FIG. 6A and FIG. 6B illustrate a time domain signal, each received by the first channel and the second channel respectively of the twin radar.
Figure 6B:
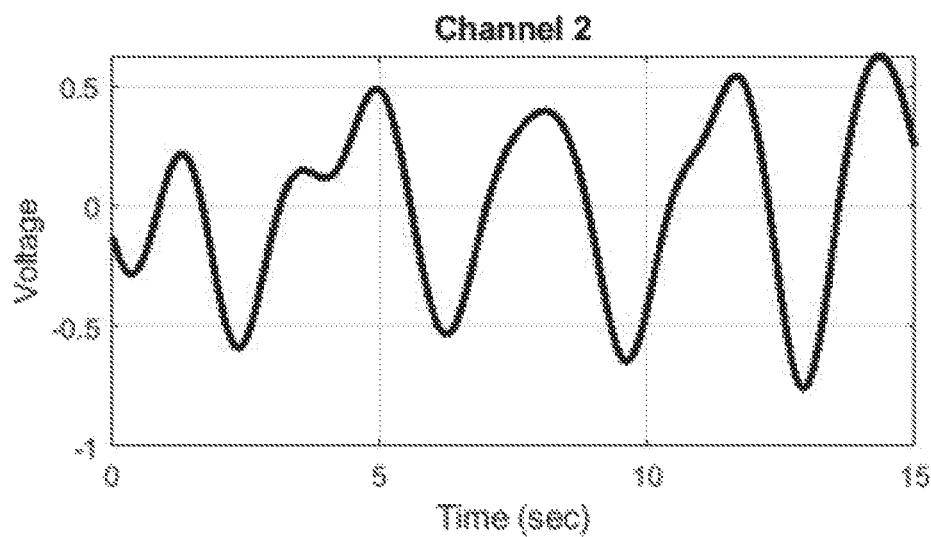
Figure 6C:
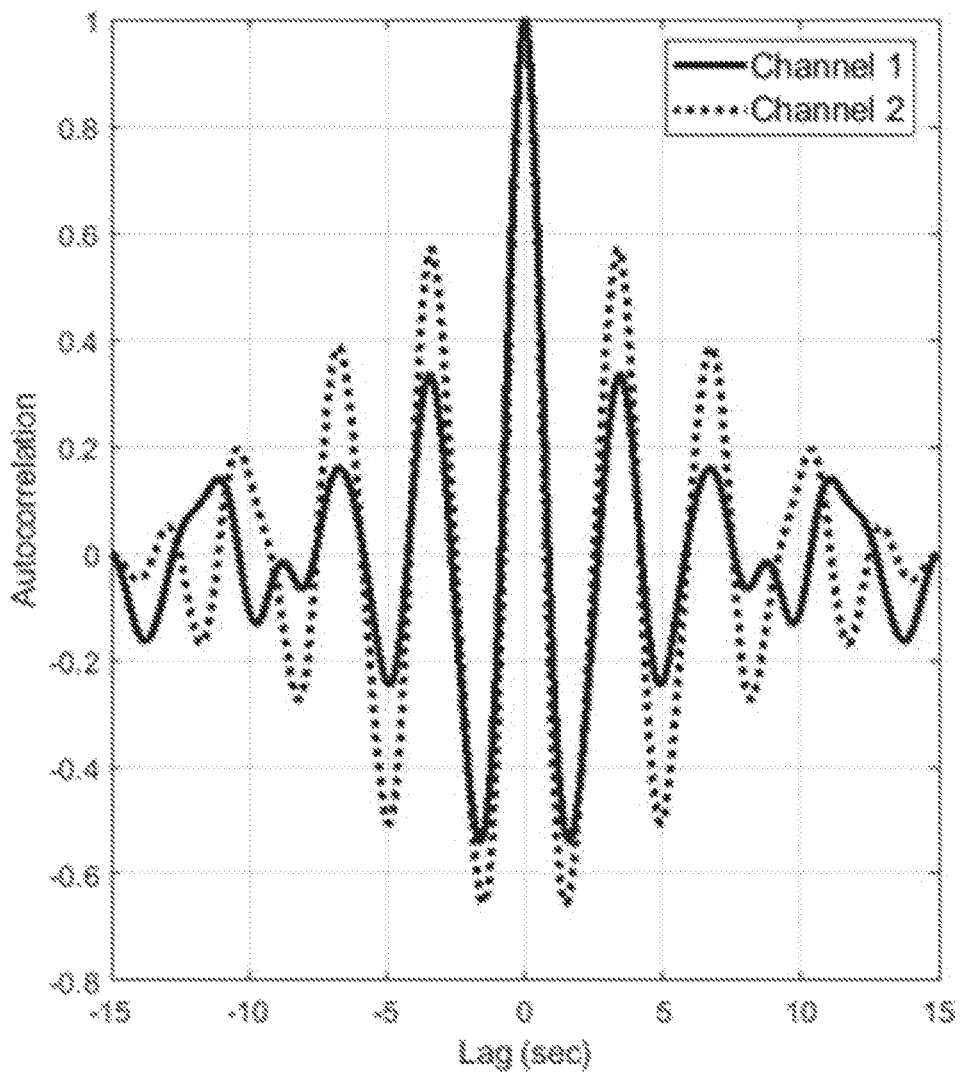
FIG. 6C illustrates autocorrelation of the time domain signals of FIG. 6A and FIG. 6B respectively, for a 15 second window, in accordance with some embodiments of the present disclosure, wherein the autocorrelation of the second channel is greater than the autocorrelation of the first channel.

FIG. 6A and FIG. 6B illustrate a time domain signal, each received by a first channel and a second channel respectively of the twin radar. FIG. 6C illustrates autocorrelation of the time domain signals of FIG. 6A and FIG. 6B respectively, for a 15 second window, in accordance with some embodiments of the present disclosure. A conflict scenario is depicted in FIG. 6A through FIG. 6C. Channel 2 has a periodic signal or the autocorrelation of the second channel is greater but the peak to peak amplitude of channel 1 is higher. Method 1 identifies channel 2 as a first potential optimum channel while method 2 identifies channel 1 as a second potential optimum channel. In accordance with the present disclosure, channel 2 with lesser variance of peak amplitudes is selected as the optimum channel.

It may be understood by persons skilled in the art that variance alone may not be sufficient to decide whether a channel is optimum or not. For instance, based on radar physics, a channel with higher peak to peak amplitude is considered as the optimum channel. There may be a scenario wherein the autocorrelation for that channel is also higher. It is quite possible that it may have a higher variance and hence may not be considered an optimum channel if the variance is checked at the outset for selecting the optimum channel.

Figure 7A:
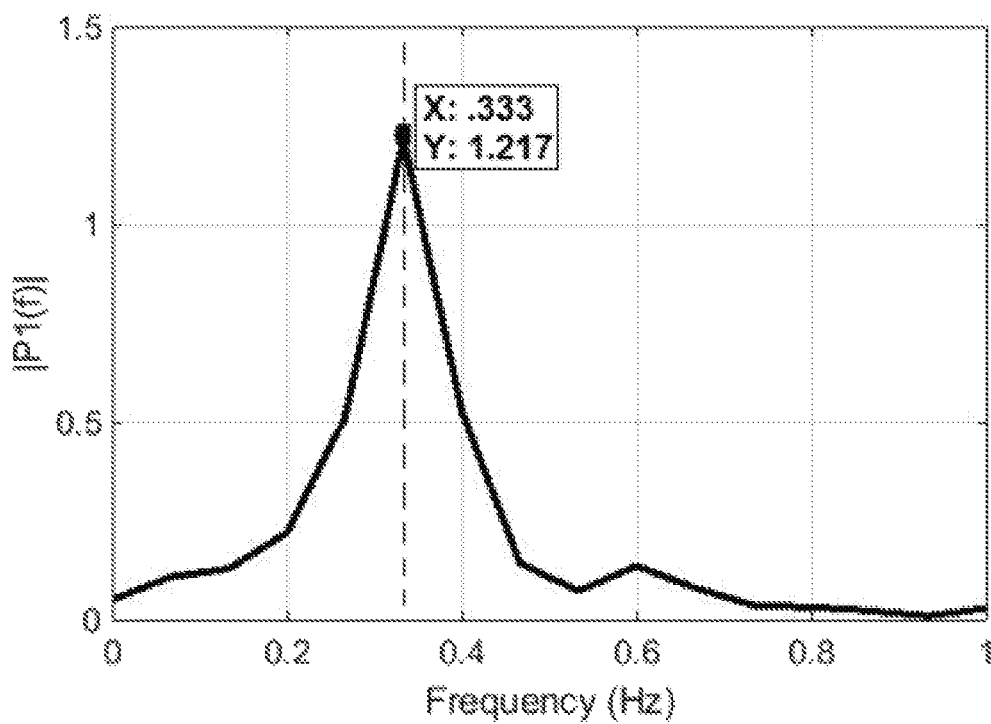
FIG. 7A illustrates a frequency spectrum of the selected optimum channel, in accordance with some embodiments of the present disclosure.
Figure 7B:
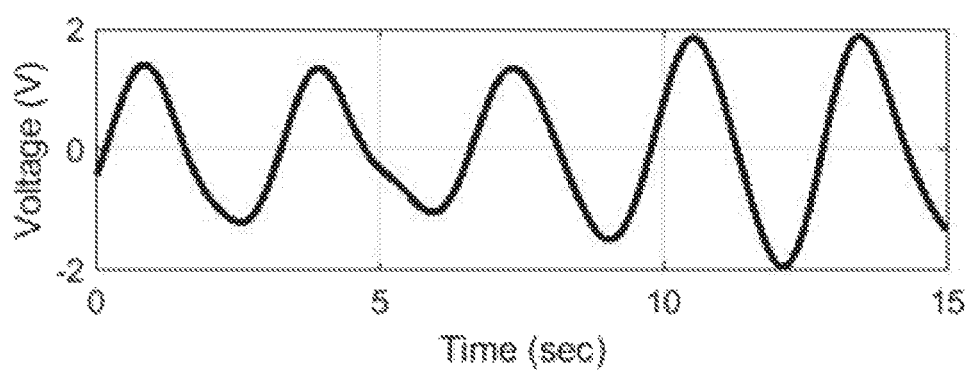
FIG. 7B illustrates the time domain signal associated with the selected optimum channel, in accordance with some embodiments of the present disclosure.

FIG. 7A illustrates a frequency spectrum of the selected optimum channel, in accordance with some embodiments of the present disclosure. FIG. 7B illustrates the time domain signal associated with the selected optimum channel, in accordance with some embodiments of the present disclosure. From FIG. 7A, the highest peak for the window is at a frequency 0.33 Hz. This calculates to 5 breaths per 15 second window.

Figure 8:
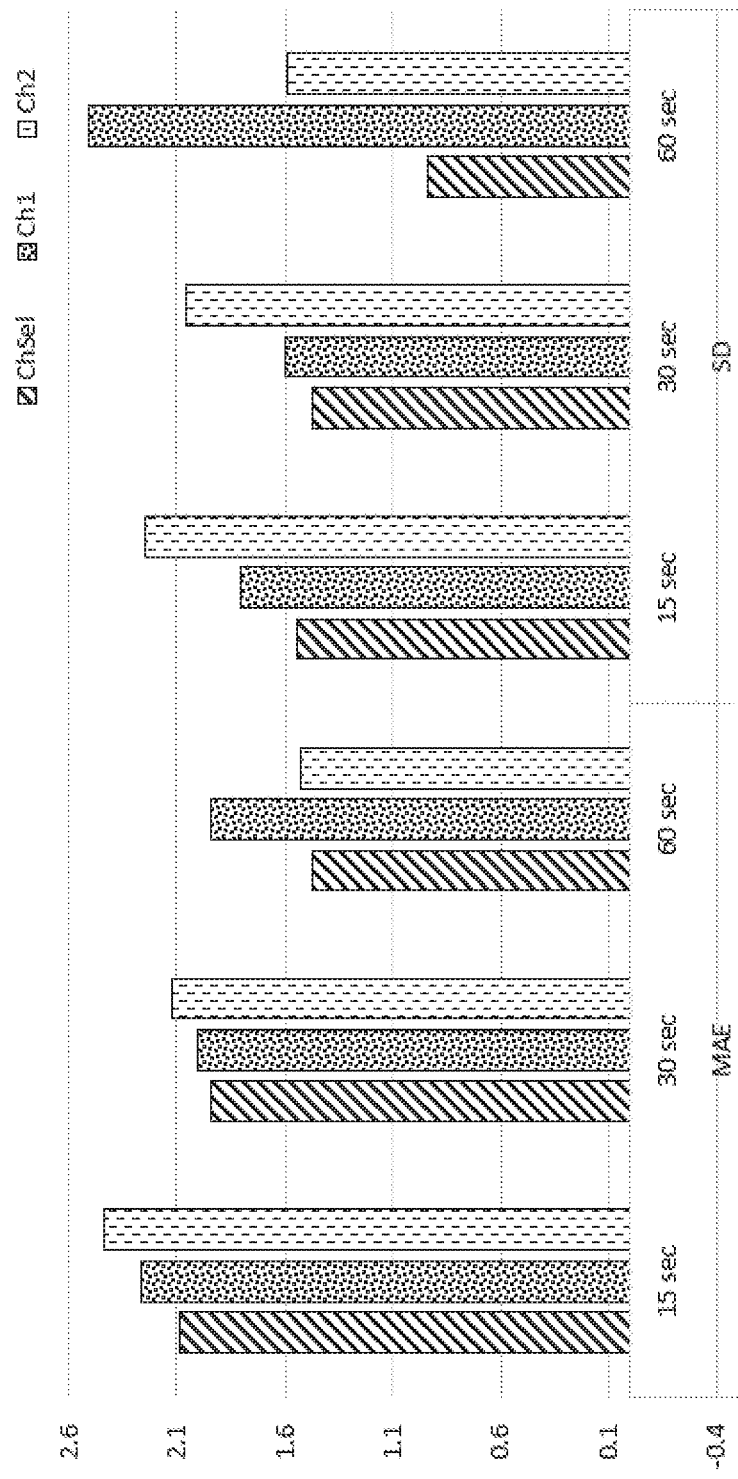
FIG. 8 illustrates Mean Absolute Error and Standard Deviation for the selected optimum channel, in accordance with some embodiments of the present disclosure.

FIG. 8 illustrates Mean Absolute Error (MAE) and Standard Deviation (SD) for the selected optimum channel (ChSel), in accordance with some embodiments of the present disclosure. It may be seen that, the MAE and its SD for the selected optimum channel is the least as compared to channel 1 (Ch1) and channel 2 (Ch2) independently for every time window. For 15 second windows, MAE (±SD) is 2.17 (±1.47), 2.29 (±1.94), and 2.65 (±1.53); for 30 second windows, it 1.94 (±1.45), 2 (±1.57) and 2.16 (±2.02) and for 60 second windows, it is 1.47 (±0.91), 1.94 (±2.44) and 1.53 (±1.53) for the method of the present disclosure, channel 1 and channel 2 respectively.

In accordance with the present disclosure, as seen from the experimental evaluation also, the steps of the method 400 are independent of the predefined time window, thereby making the method 400 window adaptive. Again, method 1 of the present disclosure is a signal property based method while method 2 of the present disclosure is a radar physics based method, making the use of the combination non-obvious to a person skilled in the art. Again, the additional elements of receiving the time domain signal reflected from the subject being monitored and filtering of the received time domain signal use the mathematical computations of method 1 and method 2 in a meaningful way such that the claim as a whole is more than a drafting effort to monopolize the mathematical computation. In particular, the combination of additional elements use the mathematical computations in a specific manner that sufficiently limits the use of the mathematical concepts to the practical application of selecting the optimum channel. Furthermore, selection of the optimum channel is independent of any hardware or software based prior calibration or data dependency or learning.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for optimum channel selection in a twin radar characterized by a first channel and a second channel, the method comprising the steps of:
    receiving a time domain signal reflected from a subject being monitored, by each of the first channel and the second channel respectively;
    filtering, by a low pass filter, the time domain signal received by each of the first channel and the second channel respectively, to obtain a filtered time domain signal having frequencies less than a predetermined frequency corresponding to restful breathing associated with the subject being monitored;
    simultaneously computing, via one or more hardware processors,
        a peak to peak value ($A_{PP1}$) of an autocorrelation function (ACF) of the filtered time domain signal associated with the first channel and the second channel respectively, for a predefined time window; and
        an average value ($V_{PP1}$) of peak to peak amplitude of the filtered time domain signal associated with the first channel and the second channel respectively, for the predefined time window; and
    selecting, via the one or more hardware processors, either the first channel or the second channel as the optimum channel based on the computed peak to peak value of the ACF and the average value of the peak to peak amplitude of the filtered time domain signal, wherein the step of selecting either the first channel or the second channel as the optimum channel comprises:
    comparing the peak to peak value ($A_{PP1}$) associated with the first channel and the second channel, respectively and selecting a channel associated with a higher peak to peak value of the ACF as a first potential optimum channel;
    comparing the average value ($V_{PP1}$) associated with the first channel and the second channel, respectively and selecting a channel associated with a higher average value of the peak to peak amplitude of the voltage signal as a second potential optimum channel; and
    performing one of:
        if the first potential optimum channel and the second potential optimum channel are identical, selecting an associated channel as the optimum channel; or
        computing variance of peak amplitudes associated with the first potential optimum channel and the second potential optimum channel and selecting a channel associated with a lesser variance of peak amplitudes as the optimum channel.

2. The processor implemented method of claim 1, further comprising performing, via the one or more hardware processors, spectrum analyses on the selected optimum channel to obtain breathing rate of the subject being monitored by:
    transforming the filtered time domain signal associated with the selected optimum channel to a frequency domain signal using a Fast Fourier transform (FFT) method; and
    obtaining the breathing rate of the subject being monitored in breaths per minute, based on a frequency associated with a highest peak of the frequency domain signal.

3. The processor implemented method of claim 1, further comprising performing, via the one or more hardware processors, spectrum analyses on the selected optimum channel to obtain heart rate of the subject being monitored by:
    filtering the time domain signal received by the selected optimum channel, by a band pass filter to obtain a filtered time domain signal having frequencies in a predetermined range corresponding to restful heart rate range associated with the subject being monitored;
    transforming the filtered time domain signal associated with the selected optimum channel to a frequency domain signal using a Fast Fourier transform (FFT) method; and
    obtaining the heart rate of the subject being monitored in beats per minute, based on a frequency associated with a highest peak of the frequency domain signal.

4. A system for optimum channel selection in a twin radar characterized by a first channel and a second channel, the system comprising: one or more data storage devices operatively coupled to one or more hardware processors and configured to store instructions configured for execution via the one or more hardware processors to:
    receive a time domain signal reflected from a subject being monitored, by each of the first channel and the second channel respectively;
    filter, by a low pass filter, the time domain signal received by each of the first channel and the second channel respectively, to obtain a filtered time domain signal having frequencies less than a predetermined frequency corresponding to restful breathing associated with the subject being monitored;

simultaneously compute:
  a peak to peak value ($A_{PP1}$) of an autocorrelation function (ACF) of the filtered time domain signal associated with the first channel and the second channel respectively, for a predefined time window; and
  an average value ($V_{PP1}$) of peak to peak amplitude of the filtered time domain signal associated with the first channel and the second channel respectively, for the predefined time window; and select either the first channel or the second channel as the optimum channel based on the computed peak to peak value of the ACF and the average value of the peak to peak amplitude of the filtered time domain signal, wherein the one or more processors are further configured to select either the first channel or the second channel as the optimum channel by:

comparing the peak to peak value ($A_{PP1}$) associated with the first channel and the second channel, respectively and selecting a channel associated with a higher peak to peak value of the ACF as a first potential optimum channel;

comparing the average value ($V_{PP1}$) associated with the first channel and the second channel, respectively and selecting a channel associated with a higher average value of the peak to peak amplitude of the voltage signal as a second potential optimum channel; and performing one of:
  if the first potential optimum channel and the second potential optimum channel are identical, selecting an associated channel as the optimum channel; or
  computing variance of peak amplitudes associated with the first potential optimum channel and the second potential optimum channel and selecting a channel associated with a lesser variance of peak amplitudes as the optimum channel.

5. The system of claim 4, wherein the one or more processors are further configured to perform spectrum analyses on the selected optimum channel to obtain breathing rate of the subject being monitored by:
  transforming the filtered time domain signal associated with the selected optimum channel to a frequency domain signal using a Fast Fourier transform (FFT) method; and
  obtaining the breathing rate of the subject being monitored in breaths per minute, based on a frequency associated with a highest peak of the frequency domain signal.

6. The system of claim 4, wherein the one or more processors are further configured to perform spectrum analyses on the selected optimum channel to obtain heart rate of the subject being monitored by:
  filtering the time domain signal received by the selected optimum channel, by a band pass filter to obtain a filtered time domain signal having frequencies in a predetermined range corresponding to restful heart rate range associated with the subject being monitored;
  transforming the filtered time domain signal associated with the selected optimum channel to a frequency domain signal using a Fast Fourier transform (FFT) method; and
  obtaining the heart rate of the subject being monitored in beats per minute, based on a frequency associated with a highest peak of the frequency domain signal.

7. A computer program product comprising a non-transitory computer readable medium having a computer readable program embodied therein, wherein the computer readable program, when executed on a computing device, causes the computing device to:
  receive a time domain signal reflected from a subject being monitored, by each of the first channel and the second channel respectively;
  filter, by a low pass filter, the time domain signal received by each of the first channel and the second channel respectively, to obtain a filtered time domain signal having frequencies less than a predetermined frequency corresponding to restful breathing associated with the subject being monitored;
  simultaneously compute, via one or more hardware processors,
    a peak to peak value ($A_{PP1}$) of an autocorrelation function (ACF) of the filtered time domain signal associated with the first channel and the second channel respectively, for a predefined time window; and
    an average value ($V_{PP1}$) of peak to peak amplitude of the filtered time domain signal associated with the first channel and the second channel respectively, for the predefined time window; and
  select, via the one or more hardware processors, either the first channel or the second channel as the optimum channel based on the computed peak to peak value of the ACF and the average value of the peak to peak amplitude of the filtered time domain signal, wherein the step of selecting either the first channel or the second channel as the optimum channel comprises:
    comparing the peak to peak value ($A_{PP1}$) associated with the first channel and the second channel, respectively and selecting a channel associated with a higher peak to peak value of the ACF as a first potential optimum channel;
    comparing the average value ($V_{PP1}$) associated with the first channel and the second channel, respectively and selecting a channel associated with a higher average value of the peak to peak amplitude of the voltage signal as a second potential optimum channel; and
    performing one of:
      if the first potential optimum channel and the second potential optimum channel are identical, selecting an associated channel as the optimum channel; or
      computing variance of peak amplitudes associated with the first potential optimum channel and the second potential optimum channel and selecting a channel associated with a lesser variance of peak amplitudes as the optimum channel.

8. The computer program product of claim 7, wherein the computer readable program further causes the computing device to perform spectrum analyses on the selected optimum channel to obtain breathing rate of the subject being monitored by:
  transforming the filtered time domain signal associated with the selected optimum channel to a frequency domain signal using a Fast Fourier transform (FFT) method; and
  obtaining the breathing rate of the subject being monitored in breaths per minute, based on a frequency associated with a highest peak of the frequency domain signal.

9. The computer program product of claim 7, wherein the computer readable program further causes the computing device to perform spectrum analyses on the selected optimum channel to obtain heart rate of the subject being monitored by:
- filtering the time domain signal received by the selected optimum channel, by a band pass filter to obtain a filtered time domain signal having frequencies in a predetermined range corresponding to restful heart rate range associated with the subject being monitored;
- transforming the filtered time domain signal associated with the selected optimum channel to a frequency domain signal using a Fast Fourier transform (FFT) method; and
- obtaining the heart rate of the subject being monitored in beats per minute, based on a frequency associated with a highest peak of the frequency domain signal.

\* \* \* \* \*